United States Patent [19]

Trassy

[11] 4,271,100
[45] Jun. 2, 1981

[54] APPARATUS FOR PRODUCING AN AEROSOL JET

[75] Inventor: Christian Trassy, Villeurbanne, France

[73] Assignee: Instruments S.A., Paris, France

[21] Appl. No.: 160,421

[22] Filed: Jun. 17, 1980

[30] Foreign Application Priority Data

Jun. 18, 1979 [FR] France ............................. 79 15575

[51] Int. Cl.³ ............................................. B05B 1/28
[52] U.S. Cl. ................................. 261/78 A; 239/291
[58] Field of Search ............... 261/78 A; 252/359 A; 356/300, 346; 239/291, 416.5, 424

[56] References Cited

U.S. PATENT DOCUMENTS

| | | | |
|---|---|---|---|
| 2,746,728 | 5/1956 | Pomerleau | 261/78 A X |
| 2,929,563 | 3/1960 | Jones | 252/359 A X |
| 3,416,730 | 12/1968 | Perry | 239/424 X |
| 4,162,970 | 7/1979 | Zlokarnik | 261/78 A X |

*Primary Examiner*—William A. Cuchlinski, Jr.
*Attorney, Agent, or Firm*—Haseltine and Lake

[57] ABSTRACT

Apparatus for producing an aerosol jet comprising an atomizing means and a flow of carrier gas for entraining the particles formed.

Downstream of the atomizing means, the conduit for carrying the aerosol constitutes the central passage (20) of a double nozzle (21) whose annular passage (22) receives another dry gaseous flow. This thus forms a central flow of aerosol, which is sheathed externally by a flow of dry gas.

The invention is used for the analysis of solutions by spectroscopy.

**

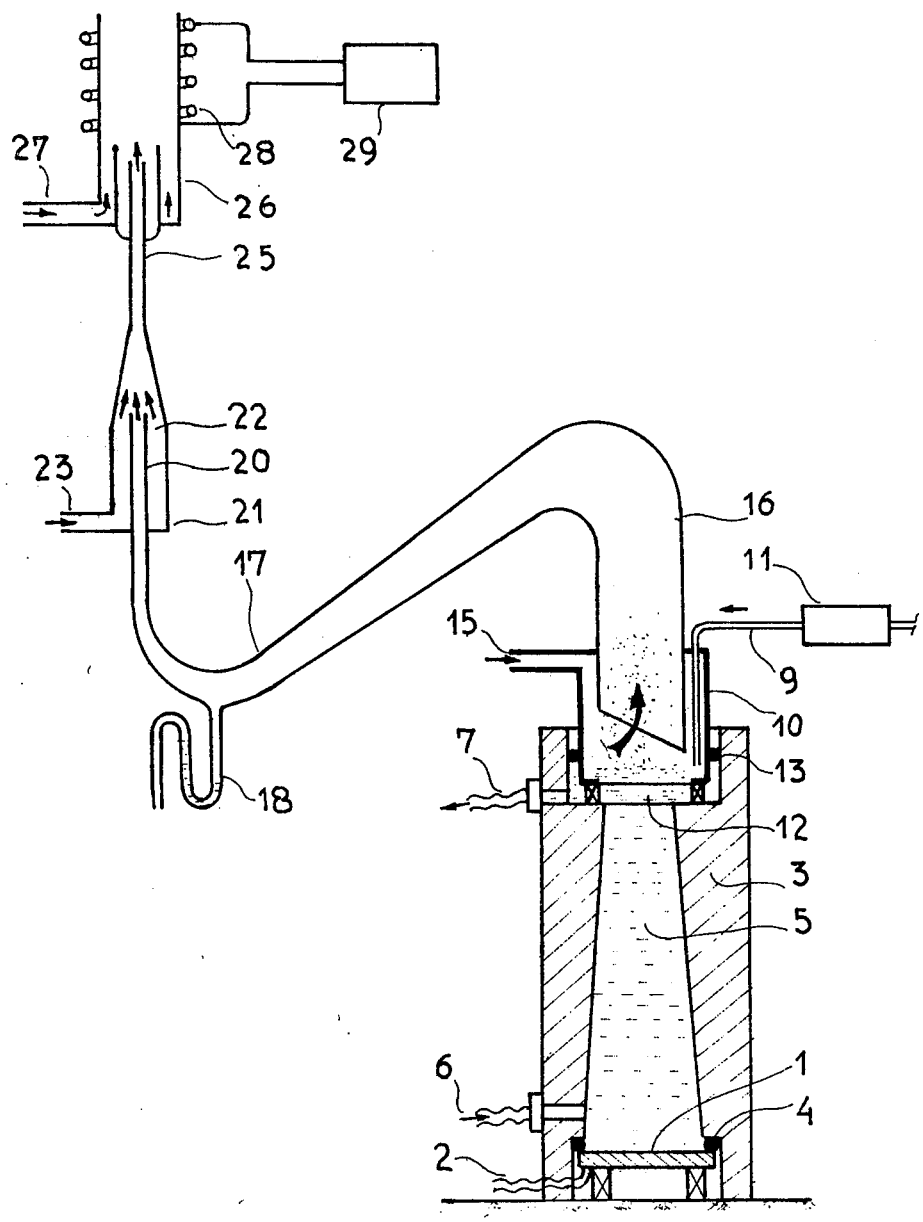

APPARATUS FOR PRODUCING AN AEROSOL JET

BACKGROUND OF THE INVENTION

The present invention concerns an apparatus for producing an aerosol jet, which is more particularly intended, by way of example, for an apparatus for analysis by spectroscopy. In an apparatus for analysing a solution by means of spectroscopy, the solution to be studied is firstly finely divided in the form of an aerosol, and then injected into a plasma flame such as of ionised argon, at a temperature of the order of 5000° C. The aerosol is excited in the plasma and in turn emits radiation which is characteristic of the elements contained in the solution. This radiation is analysed in a conventional spectrometer.

Various means are known for putting the solution into a finely divided form, and in particular the use of ultrasonics to cause the liquid mass to be broken down into very fine droplets; the droplets can then be entrained in a gas flow towards the position of use thereof and in particular towards the plasma torch. In the conventional apparatuses in their present state, certain droplets which are being transported can come into contact with the walls of the duct; in the vicinity of the plasma torch, the walls are hot, which, in that region, causes the droplets to evaporate, and the salts contained therein are deposited. This gives rise to the danger of restricting the flow section of the duct, and even blocking the duct. However, this also has the even more serious consequence of leaving in the apparatus a 'memory', which gives rise to the danger of falsifying the following analysis result, for example by a part of the deposits formed in the course of previous analysis operations being dissolved in the new mist of a subsequent analysis operation. In order to avoid such interference phenomena, the conduits for carrying the aerosol into the flame would have to be rinsed or changed for each analysis operation, which is incompatible with the increasingly felt need for the capability of carrying out sequential analysis operations at high rates.

SUMMARY OF THE INVENTION

The present invention provides a solution for overcoming such disadvantages, and makes it possible to improve the energy efficiency of the apparatus.

The invention concerns an apparatus for producing an aerosol jet, comprising a means for atomisation of the substance to be transported, with the creation of a flow of carrier gas for entraining the particles formed. According to the invention, downstream of the actual atomising means, the conduit for carrying the aerosol formed by the carrier gas and the particles in a state of suspension constitutes the central passage of a double nozzle whose annular passage receives another dry gas flow thereby to form, in the conduit for carrying the whole towards the position of use, a central flow of aerosol which is externally sheathed by a flow of dry gas, the flow rates and the relative positioning of the annular and central passages of the nozzle being so determined that the flow patterns of the two flows remain laminar and at adjacent speeds.

In accordance with a preferred embodiment, the axis of the nozzle and the conduit between the outlet of the nozzle and the position of use is vertical or only very slightly inclined.

BRIEF DESCRIPTION OF THE DRAWING

The invention will be better appreciated by referring to a particular embodiment which is given by way of example and which is shown in the accompanying drawing.

The single FIGURE is a diagrammatic view of an apparatus for atomising a solution by ultrasonic means and injecting the resulting mist into a plasma flame for analysis by spectro-emission.

DESCRIPTION OF AN EMBODIMENT

The apparatus comprises an ultrasonic generator which is formed by a piezoelectric crystal 1 which is excited electrically from a generator (not shown) to which it is connected by connections 2. The ultrasonic waves, which are in a frequency range of from 200 KHz to 10 MHz, are transmitted by a liquid column 5 which maintains a constant load on the crystal. The liquid column is maintained in a body 3 which is placed on the crystal, with the interposition of sealing joints 4, continuous circulation of water being maintained between an inlet 6 and an outlet 7 in order also to provide for cooling.

The solution to be atomised is introduced by the pipe 9 into the cell 10 by means of a peristaltic pump 11 which is actuated by a stepping motor in order to maintain a constant amount of liquid in the cell, in the course of operation of the apparatus. The cell 10 which is closed in its lower part by a thin membrane 12, for example comprising polyester which is from 10 to 100 microns in thickness, is fitted on to the body 3 with sealing joints 13 being interposed.

The cavity in the body 3 forms an impedance matching means which is intended to increase the amplitude of the acoustic wave and the production of aerosol, while also making it possible for the power to be supplied to the crystal to be reduced. The amplification effect is achieved by a reduction in section from the inlet towards the outlet; as the density of acoustic energy required for the production of cavitation in the solution is constant, the energy to be applied to the crystal will be inversely proportional to the sectional area.

The matching means is formed by a solid body (metal, glass . . . ) which has an acoustic impedance such that the coefficient of reflection of the wave at the interface between the body and the column of liquid is total. The matching means must be of a regular shape and, taking into account the fact that the dimensions are here markedly greater than the wavelength, a conical shape has been selected as being easier to produce.

The internal surface condition of the matching means must be better than a fiftieth of the wavelength in order to achieve a satisfactory degree of efficiency. In order to avoid degradation of the surface condition, which would result in a deterioration in the degree of efficiency, the transmission liquid selected is a liquid which is chemically inert with respect to the material forming the guide. Particularly when the liquid used is water, it must be demineralised and degassed, as any deposit on the internal wall surfaces of the guide gives rise to the danger of interferring with proper functioning thereof. Its temperature must be stable and must be for example lower than 17° C. when the liquid used is water.

For any question in regard to diffraction of the sound waves which may be involved in calculation of the impedance matching means, reference may be made for example to a work such as 'Fundamental of Ultrasonics', J. BLITZ, Butterworths, London.

The droplets formed by the cavitation phenomena produced by the ultrasonics in the vicinity of the surface of the solution in the cell 10 are entrained by a flow or argon which is introduced at 15. The aerosol which is thus formed is entrained into the extraction stack or funnel 16 whose base is of a bevel configuration in order to ensure that the large-diameter drops which are thrown up by the ultrasonics geyser are returned, without causing disturbances. The drops of excessively large diameter or which are re-deposited on the walls of the conduit are then recovered in the elbow-bent drain 17 provided with a discharge sylphon 18.

The aerosol is then taken by way of the central tube 20 into the double nozzle 21 whose peripheral annular conduit 22 is supplied with a dry gaseous flow which is introduced by way of the passage 23. The flow rates and the speeds on the one hand of the central flow of wet aerosol, which carries the droplets of solution, and on the other hand the annular flow of dry gas, are so determined as to maintain laminar flow patterns at similar speeds, in order to avoid the formation of eddies at their interface. This thus produces, in the outlet pipe 25, a central jet of gas carrying the wet particles of the solution, and a real continuous outer sheath of dry gas which prevents the particles being transported from coming into contact with the walls.

It is the conduit 25 which serves as a means for injecting the aerosol into the plasma torch 26 which is formed in the usual manner by an input of a flow of plasmagenic gas such as argon which is carried by the conduit 27 between the turns of an inductor 28 which is supplied at very high frequency by a generator 29.

It will be seen that, in the conduit 25 which is heated by the proximity of the torch 26, the droplets of the solution to be analysed, being in suspension in the aerosol, cannot be caused to evaporate by contact with the hot walls and deposit thereon the salts contained in the droplets. The conduit 25 therefore always remains clean and of constant section, and, at the end of an analysis operation, it is without any trace of the solution which has just been the subject of study. The apparatus can then be switched over to another analysis operation without any danger and instantly, and without requiring any dismantling or rinsing.

In order to maintain the quality of the gaseous sheathing, care will be taken to ensure that the flow formed at the outlet from the nozzle does not have any transverse components due to gravitational pull. For that purpose, the system comprising the nozzle and the outlet conduit leading to the position of use will be disposed vertically, at least when the aerosol contains particles of relatively large sizes (1 micron in regard to water) or of high densities. For light particles or particles of small sizes (less than 0.1 micron for example for water), it would be possible to tolerate short sections in which the system extends at an inclined angle or even horizontally if the flow speed makes it possible sufficiently to limit the period of time for which the particles are flowing in those portions in which the gravitational pull could cause a flow across the gaseous protective sheathing.

It will be appreciated that the invention is not limited to the single embodiment or the single use described above by way of example, but it also embraces constructions which would differ therefrom only in regard to details, design variations or by the use of equivalent means.

Thus, the invention can be applied to the production of aerosol jets whenever the danger of hot walls suffering from the deposit of particles which are being transported, is likely to be prejudicial to good preservation or good functioning of the installation. The particles may then be solid or liquid, for example for feeding burners or boilers, and atomisation of the substance to be transported by the aerosol could be effected by known means other than ultrasonics.

I claim:

1. Apparatus for producing an aerosol jet comprising a means for atomising the substance to be transported, with the creation of a flow of carrier gas to entrain the particles formed, characterised in that downstream of the actual atomising means, the conduit for carrying the aerosol formed by the carrier gas and the particles in a state of suspension constitutes the central passage (20) of a double nozzle (21) whose annular passage (22) receives another dry gas flow thereby to form, in the conduit for carrying the whole towards the position of use, a central flow of aerosol which is externally sheathed by a flow of dry gas, the flow rates and the relative positioning of the annular and central passages of the nozzle being so determined that the flow patterns of the two flows remain laminar and at adjacent speeds, and that the axis of the nozzle (20) and the conduit (25) between the outlet of the nozzle and the position of use is vertical or only very slightly inclined.

* * * * *